(12) United States Patent
Wang

(10) Patent No.: US 12,181,483 B2
(45) Date of Patent: Dec. 31, 2024

(54) KIT COMPRISING ANTIBODY BINDING ACROLEIN-PROTEIN CONJUGATE FOR DIAGNOSING NEPHROPATHY

(71) Applicant: National Yang Ming Chiao Tung University, Taipei (TW)

(72) Inventor: Hsiang-Tsui Wang, Taipei (TW)

(73) Assignee: NATIONAL YANG MING CHIAO TUNG UNIVERSITY, Taipei (TW)

(*) Notice: Subject to any disclaimer, the term of this patent is extended or adjusted under 35 U.S.C. 154(b) by 0 days.

(21) Appl. No.: 17/929,254

(22) Filed: Sep. 1, 2022

(65) Prior Publication Data

US 2024/0036058 A1 Feb. 1, 2024

(30) Foreign Application Priority Data

Apr. 27, 2022 (TW) ................... 111116068

(51) Int. Cl.
*C07K 16/18* (2006.01)
*G01N 33/68* (2006.01)

(52) U.S. Cl.
CPC ... *G01N 33/6893* (2013.01); *G01N 2800/347* (2013.01)

(58) Field of Classification Search
None
See application file for complete search history.

(56) References Cited

PUBLICATIONS

Igarashi et al. Mol. Nutr. Food Res. 55: 1332-1341, 2011.*
Screen capture: Wikipedia contributors. (Jan. 13, 2024). ELISA. In Wikipedia, The Free Encyclopedia. Retrieved 02:10, Jan. 25, 2024, from <https://en.wikipedia.org/w/index.php?title=ELISA&oldid=1195317246>).*
Boguszewska et al. (Cell. Mol. Life Sci. 76: 4689-4704, 2019).*
Hong et al. Acrolein contributes to urothelial carcinomas in patients with chronic kidney disease. Urol. Oncol. 38: 465-475, 2020.*
Takamatsu et al. A Reduction-Based Sensor for Acrolein Conjugates with the Inexpensive Nitrobenzene as an Alternative to Monoclonal Antibody. Sci Rep 6, 35872 (2016). doi.org/10.1038/srep35872.*
Tsou et al. Alterations in Acrolein Metabolism Contribute to Alzheimer's Disease. J. Alzheimer's Dis. 61: 571-580, 2018.*
Wang et al. Acrolein acts as a neurotoxin in the nigrostriatal dopaminergic system of rat: involvement of α-synuclein aggregation and programmed cell death. Sci Rep 7, 45741 (2017). doi.org/10.1038/srep45741.*
Wang et al. Acrolein preferentially damages nucleolus eliciting ribosomal stress and apoptosis in human cancer cells. Oncotarget. 7 (49): 80450-80464, 2016.*
Yoshida et al. Identification of acrolein-conjugated protein in plasma of patients with brain infarction. Biochem. Biophys. Res. Comm. 391: 1234-1239, 1010.*

* cited by examiner

*Primary Examiner* — Christine J Saoud
(74) *Attorney, Agent, or Firm* — MUNCY, GEISSLER, OLDS & LOWE, P.C.

(57) ABSTRACT

A biomarker includes acrolein-protein conjugate (Acr-PC). An assay kit includes an antibody capable of binding to the biomarker for diagnosing nephropathy, monitoring the progression of nephropathy, or assessing the therapeutic response of nephropathy. The antibody includes a heavy chain having the amino acid sequence of SEQ ID NO:1 and a light chain having the amino acid sequence of SEQ ID NO:2.

1 Claim, 13 Drawing Sheets

Specification includes a Sequence Listing.

SEQUENCE LISTING

```
Sequence total quantity: 2
SEQ ID NO: 1            moltype = AA   length = 132
FEATURE                 Location/Qualifiers
source                  1..132
                        mol_type = protein
                        organism = Mus musculus
SEQUENCE: 1
QVQLQESGAE LARPGASVRL SCKASGNIFP DHSINWVKQR TGQGLEWIGE IFHGSGNTYY    60
NEKFKGKATL TADKSSTTVY LQLTSLTSED SAVYFCARWV YGSSFFDVWG AGTTVTVSSA   120
KTTPPSVYPL AP                                                      132

SEQ ID NO: 2            moltype = AA   length = 119
FEATURE                 Location/Qualifiers
source                  1..119
                        mol_type = protein
                        organism = Mus musculus
SEQUENCE: 2
DIVLTQTPAS LAVSLGQTIT IFCRASESVE YYGTNLMQWY QQKPGQPPRV LIYGASNVES    60
GVPARFSGSG SGTDFSLNIL PVEEDDIAMY FCQQSRKVPW TFGGGTKLEI KRADAAPTV   119
```

KIT COMPRISING ANTIBODY BINDING ACROLEIN-PROTEIN CONJUGATE FOR DIAGNOSING NEPHROPATHY

CROSS-REFERENCE TO RELATED APPLICATIONS

This application claims priority in Taiwan Patent Application No. 111116068, filed on Apr. 27, 2022, which is incorporated by reference in its entirety herein.

REFERENCE TO AN ELECTRONIC SEQUENCE LISTING

The contents of the electronic sequence listing (2022-09-01_SeqListing.xml; Size: 3,019 bytes; and Date of Creation: 2022 Jul. 15) is herein incorporated by reference in its entirety.

FIELD OF THE INVENTION

This disclosure relates to acrolein-protein conjugate (Acr-PC) as a kidney disease biomarker. Mainly, a method for diagnosing kidney diseases and a kit comprises an antibody that can recognize acrolein-protein conjugate (Acr-PC). The antibody that recognizes acrolein-protein conjugate (Acr-PC) can be used as a non-invasive diagnostic method for nephropathy and to monitor the progression of nephropathy.

BACKGROUND OF THE INVENTION

Diabetic nephropathy (DN), or diabetic kidney disease, is a major chronic complication of diabetes. It is the most frequent cause of chronic kidney disease (CKD) and end-stage renal disease (ESRD) globally. Despite developing advancements in controlling diabetic nephropathy, the prevalence of CKD with diabetes is the same today as it was 20 years ago. The current strategy to manage DN is helpful in the early stages of DN. However, the results are uncertain in patients with relatively advanced CKD. The purpose of treatment should be to delay disease progression and eventual treatment failure. Therefore, early diagnosis is critical in reducing the individual and socioeconomic burdens associated with DN by providing appropriate management to prevent the development and progression of this condition.

Generally, evaluating kidney function using estimated glomerular filtration rate (eGFR) and assessing kidney damage using albuminuria are two diagnostic methods to identify and monitor DN. However, these markers have numerous limitations. Although the eGFR, the best overall index of kidney function, is used widely to screen and monitor for CKD, including DN, it has been reported to underestimate the renal function in some populations, particularly in patients with near-normal renal function. On the other hand, albuminuria is considered a sensitive marker of CKD and is used as the first clinical indicator of DN. However, there are limitations in using albuminuria as a marker of DN, as many patients experience eGFR loss without deterioration in albuminuria or even normoalbuminuria. Histologically proven advanced diabetic glomerular lesions can develop regardless of normoalbuminuria. Furthermore, low-grade albuminuria is a weaker predictor of disease progression than macroalbuminuria. Therefore, some serum or urinary biomarkers can potentially provide a basis for developing improved diagnostic tests other than those based on albuminuria.

Hyperglycemia (the elevation of blood glucose) is an important characteristic of diabetes patients and is the principal cause of diabetes-associated complications, including DN. According to recent studies, hyperglycemia-induced activation of the electron transport chain can increase the reactive oxygen species (ROS) production, which is thought to initiate the development of complications in diabetes. In DN patients, hyperglycemia and hemodynamic alterations, especially activation of the renin-angiotensin system (RAS), trigger various cell signaling cascades, including the MAPKs (p38 and JNK) and PKC-$\beta$ pathways. In response to these signals, renal cells, such as tubular epithelial cells, podocytes, and mesangial cells, can produce chemokines, growth factors, and profibrotic cytokines resulting in monocyte/macrophage differentiation, proliferation, and activation. Activated macrophages can produce proinflammatory and profibrotic cytokines, ROS, and antiangiogenic factors, contributing to a cycle of inflammation, oxidative stress, cellular injury, progressive fibrosis, and damaged glomerular filtration rate. Podocyte loss, endothelial dysfunction, alterations in the glomerular basement membrane, and tubular damage increase proteinuria during the development and progression of DN.

Acrolein, an $\alpha,\beta$-unsaturated aldehyde, is a common dietary and environmental pollutant. Additionally, acrolein is endogenously generated during lipid peroxidation, amine oxidase-mediated polyamine metabolism, and myeloperoxidase production. The main route of acrolein elimination involves the production of S-(3-hydroxypropyl)-N-acetylcysteine (3-HPMA) in conjunction with glutathione (GSH), the primary metabolite of acrolein found in urine, and GSH has been identified as a protective scavenger of acrolein. The free form of acrolein reacts with proteins to form acrolein protein conjugate (Acr-PC), resulting in the inactivation of proteins and tissue injury. Previous studies have shown that acrolein is associated with diabetes and its complications, including diabetic retinopathy and diabetic neuropathy. Furthermore, it has been shown that acrolein is produced as a fatty acid product due to free radicals generated from the glucose auto-oxidation process during hyperglycemia, which may lead to tissue injury and is one of the initial problems to be linked to high levels of glucose in vivo. Additionally, it is well established that polyamines (putrescine, spermidine, and spermine) are necessary for cell growth: however, acrolein is produced from polyamines and has been suggested to be one of the uremic "toxins," which accelerates the progression of uremia. The level of acrolein produced from spermine is correlated with the degree of chronic renal failure. Our previous study showed that plasma Acr-PC levels were elevated in CKD patients. However, the role of acrolein in diabetic nephropathy remains unclear. In the present invention, we investigated the pathogenic role of acrolein in DN using in vivo and in vitro DN models. Furthermore, the potential of acrolein scavengers as therapeutic strategies were also examined. This study provides insights into early detection, prevention, and treatment strategies for DN patients.

Accordingly, it is essential to develop a fast and effective non-invasive diagnostic method for nephropathy patients or those at risk of nephropathy. The present invention provides a kit that can identify acrolein-protein conjugate (Acr-PC) comprising the antibody, which can recognize the Acr-PC biomarker.

SUMMARY OF THE INVENTION

Given the problem mentioned earlier, the present invention provides an acrolein-protein conjugate (Acr-PC) biomarker and a non-invasive diagnostic kit or/and a non-invasive diagnostic method for diagnosing nephropathy, monitoring the progression of nephropathy, or assessing the therapeutic response of nephropathy.

In one embodiment, a biomarker for diagnosing nephropathy, monitoring the progression of nephropathy, or assessing the therapeutic response of nephropathy is acrolein-protein conjugate (Acr-PC).

In one embodiment, a kit for diagnosing nephropathy, monitoring the progression of nephropathy, or assessing the therapeutic response of nephropathy, comprising an antibody that can recognize the Acr-PC biomarker.

In one embodiment, the antibody is consisting of a heavy chain (SEQ ID NO:1) and a light chain (SEQ ID NO:2), wherein the 7 to 128 amino acid residue of the heavy chain is the critical region for recognizing the biomarker; wherein the 8 to 119 amino acid residue of the light chain is the critical region for recognizing the biomarker.

Sequences of the heavy chain (SEQ ID NO:1) of the antibody which can be employed in accordance with the invention are shown herein below:

SEQ ID NO: 1:
QVQLQESGAELARPGASVRLSCKASGNIFPDHSINWVKQRTGQGLEWIG
EIFHGSGNTYYNEKFKGKATLTADKSSTTVYLQLTSLTSEDSAVYFCAR
WVYGSSFFDVWGAGTTVTVSSAKTTPPSVYPLAP

Sequences of the light chain (SEQ ID NO:2) of the antibody which can be employed in accordance with the invention are shown herein below:

SEQ ID NO: 2
DIVLTQTPASLAVSLGQTITIFCRASESVEYYGTNLMQWYQQKPGQPPR
VLIYGASNVESGVPARFSGSGSGTDFSLNILPVEEDDIAMYFCQQSRKV
PWTFGGGTKLEIKRADAAPTV

BRIEF DESCRIPTION OF THE DRAWINGS

FIG. 4A shows the chemical reaction of Na-acetyl-lysine and acrolein to form Na-acetyl-FDP-lysine as Acr-PC standards (STD).

FIGS. 4B-4C show a typical LC/MS/MS chromatogram for Na-acetyl-FDP-lysine. FIG. 4B shows that the retention time (RT) of the Na-acetyl-FDP-lysine eluted at 0.91 min. FIG. 4C shows the chromatogram representing the Na-acetyl-FDP-lysine (283.0→83.35 m/z transition. The amount of Na-acetyl-FDP-lysine was calculated by taking the ratio of the two peak areas and multiplying it by the amount of standard.

FIG. 4D shows that the linear calibration curve of Na-acetyl-FDP-lysine was obtained using a peak area ratio of 6 standards (3.13, 6.25, 12.5, 25, 50, and 100 μM) as a function of the different concentrations.

DETAILED DESCRIPTION OF THE INVENTION

Figure 1:
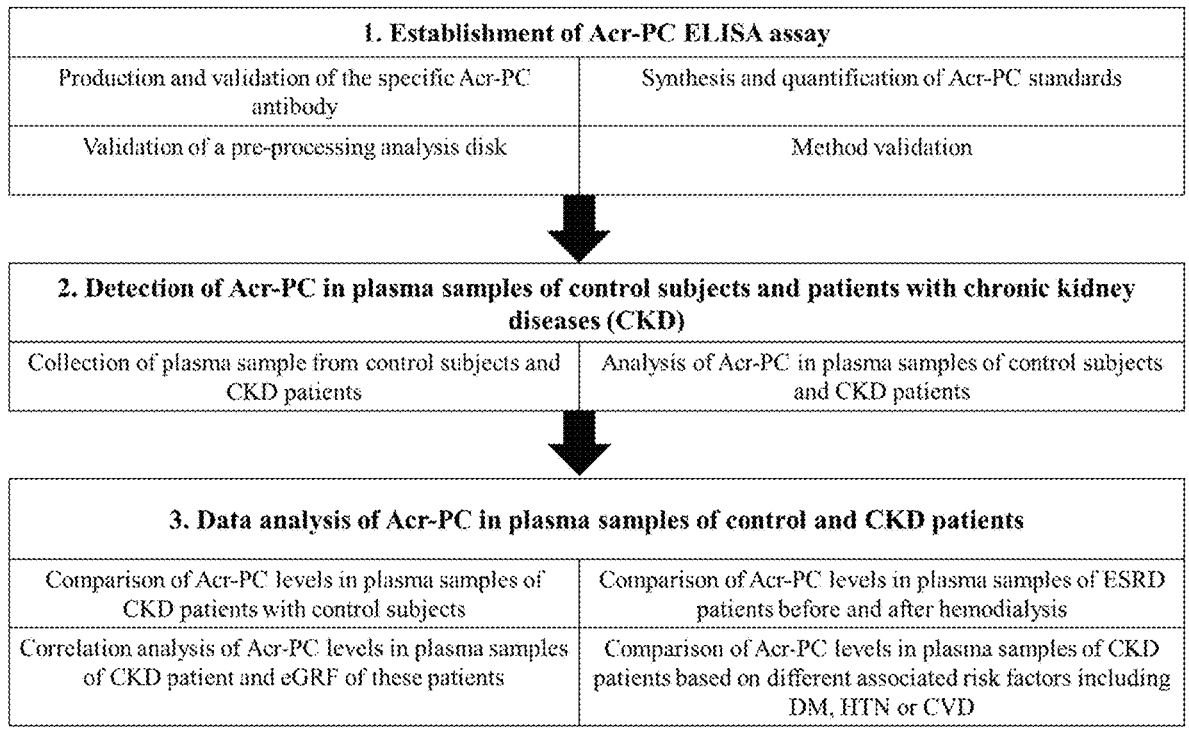
FIG. 1 shows the flow chart of the present invention.

The present invention provides acrolein-protein conjugate (Acr-PC) as a biomarker for diagnosing nephropathy, monitoring the progression of nephropathy, or assessing the therapeutic response of nephropathy.

Further, the present invention provides an antibody with the Acr-PC binding specificity can recognize the Acr-PC biomarker. Therefore, the antibody can be used for diagnosing nephropathy, monitoring the progression of nephropathy, or assessing the therapeutic response of nephropathy.

Further, the present invention provides a kit for diagnosing nephropathy, monitoring the progression of nephropathy, or assessing the therapeutic response of nephropathy, comprising an antibody that can recognize the Acr-PC biomarker in the present invention and pre-processing analysis disk, wherein the pre-processing analysis disk is prepared for a competitive ELISA. The antibody is consisting of a heavy chain (SEQ ID NO:1) and a light chain (SEQ ID NO:2), wherein 7 to 128 amino acid residues of the heavy chain is the critical region for recognizing the biomarker: wherein 8 to 119 amino acid residues of the light chain is the critical region for recognizing the biomarker. The kit can detect the expression of the biomarker in subjects by an immunoassay, wherein the biomarker is Acr-PC: wherein the immunoassay can be ELISA.

Sequences of the heavy chain (SEQ ID NO: 1) of the antibody which can be employed in accordance with the invention are shown herein below:

SEQ ID NO: 1:
QVQLQESGAELARPGASVRLSCKASGNIFPDHSINWVKQRTGQGLEWIG
EIFHGSGNTYYNEKFKGKATLTADKSSTTVYLQLTSLTSEDSAVYFCAR
WVYGSSFFDVWGAGTTVTVSSAKTTPPSVYPLAP

Sequences of the light chain (SEQ ID NO:2) of the antibody which can be employed in accordance with the invention are shown herein below:

SEQ ID NO: 2
DIVLTQTPASLAVSLGQTITIFCRASESVEYYGTNLMQWYQQKPGQPPR
VLIYGASNVESGVPARFSGSGSGTDFSLNILPVEEDDIAMYFCQQSRKV
PWTFGGGTKLEIKRADAAPTV

Further, the present invention provides a method for diagnosing nephropathy, monitoring the progression of nephropathy, or assessing the therapeutic response of nephropathy, the method comprises the steps of:
(a) Providing a kit in the present invention for diagnosing nephropathy,
(b) Detecting the expression of a biomarker of a subject; and
(c) Comparing the expression of the biomarker of the subject with a control sample, wherein the control sample is from a healthy subject who does not suffer from chronic kidney disease (CKD); wherein when the expression of the biomarker of the subject is 2.4 times higher than the control sample of the healthy subject who does not suffer from CKD, the subject has a risk of developing nephropathy: wherein when the expression of the biomarker of the subject is 4 times higher than the control sample of the healthy subject which does not suffer from CKD, the subject has the risk of dialysis, wherein the CKD means eGFR<60 ml/min/1.73 m$^2$, belong to 3-5 stage CKD clinically, wherein the biomarker is Acr-PC.

Additional specific embodiments of the present invention include, but are not limited to the following:

Example 1

Figure 2A:
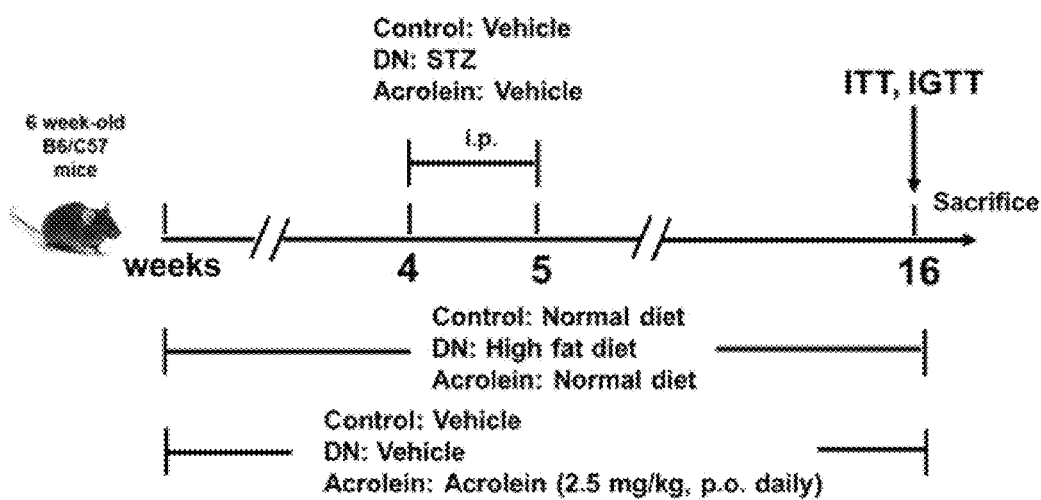
FIG. 2A shows the experimental design scheme of the diabetic nephropathy (DN) and the acrolein-treated animal models.
Figure 2B:
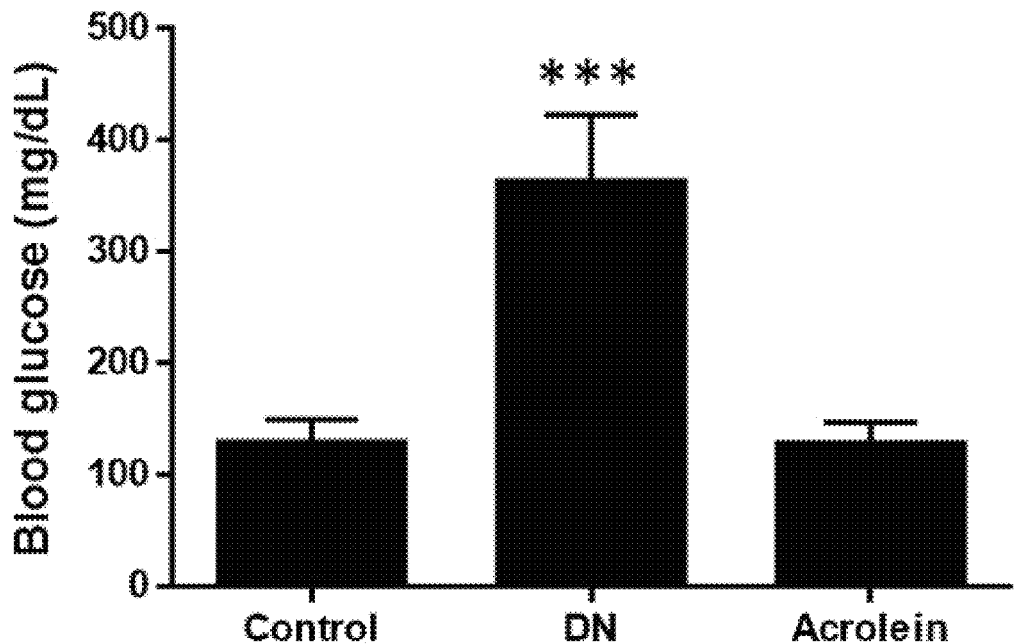
FIG. 2B shows the fasting plasma glucose of the control group, the diabetic nephropathy (DN) group, and the acrolein group after 16 weeks.
Figure 2C:
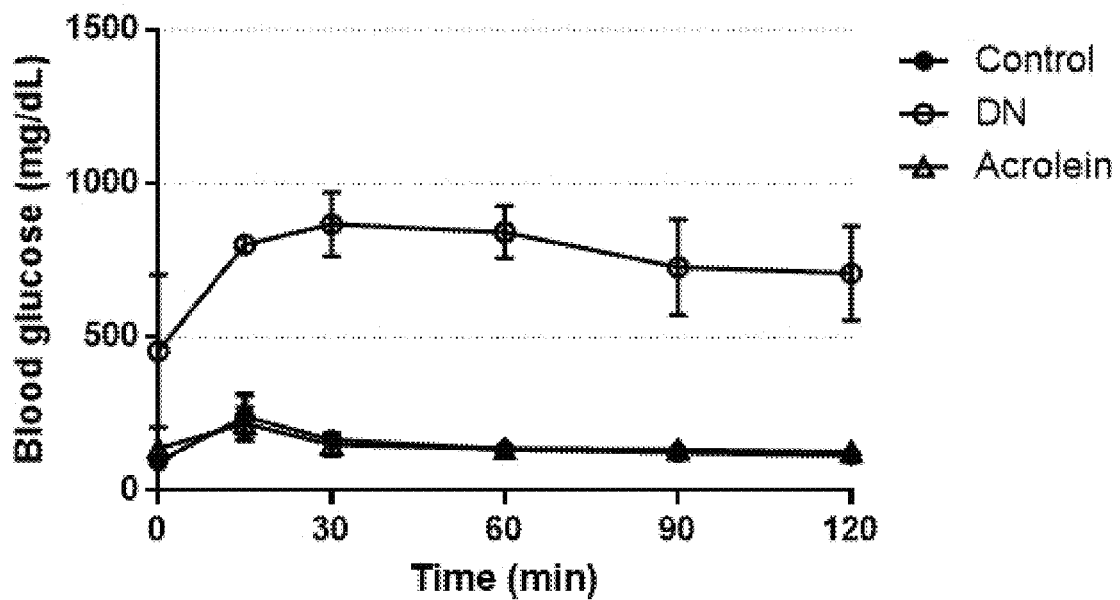
FIG. 2C shows the intraperitoneal glucose tolerance tests (IGTT) of the control group, the diabetic nephropathy (DN) group, and the acrolein group after 16 weeks.
Figure 2D:
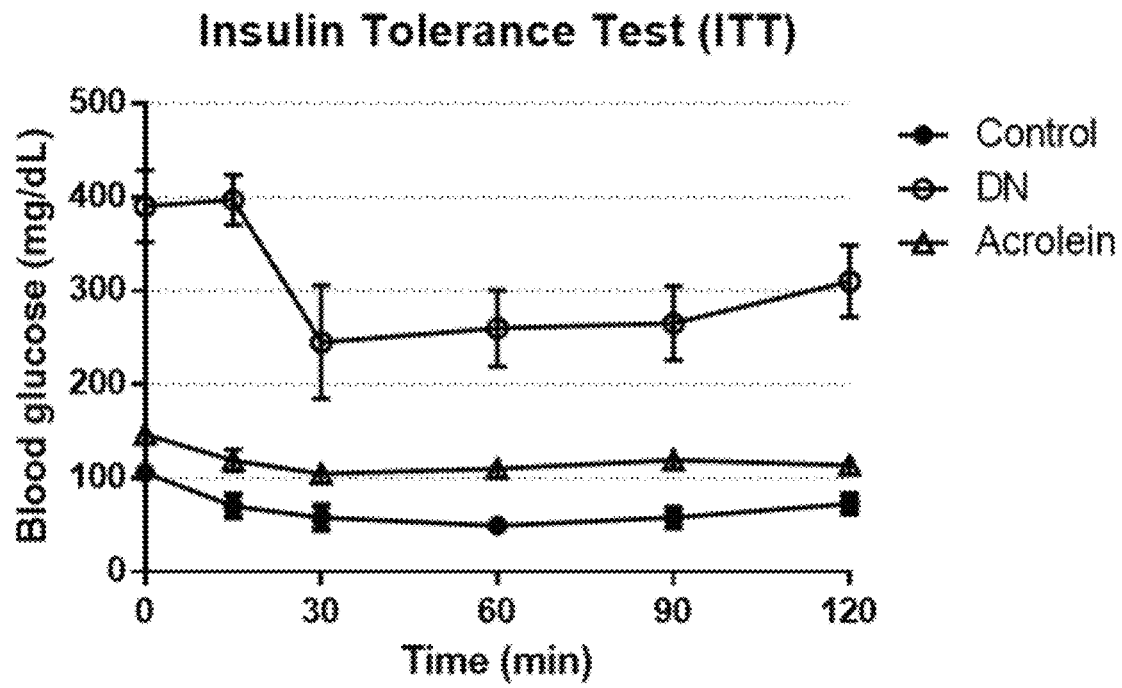
FIG. 2D shows the insulin tolerance tests (ITT) of the control group, the diabetic nephropathy (DN) group, and the acrolein group after 16 weeks.
Figure 2E:
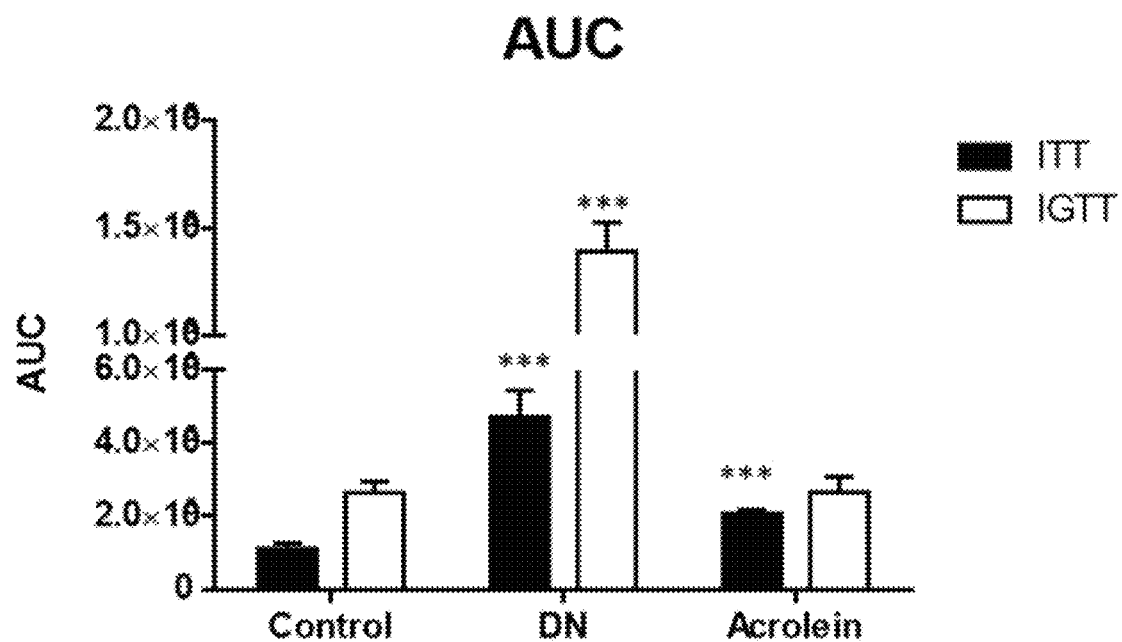
FIG. 2E shows the area under the curve (AUC) quantification for IGTT and ITT of the control group, the diabetic nephropathy (DN) group, and the acrolein group after 16 weeks.

Detecting the Expression of Acr-PC in Kidney Tissues from a Diabetic Nephropathy Animal Model and an Acrolein-Treated Animal Model To investigate the role of acrolein in the pathogenesis of diabetic nephropathy (DN), we compared the renal function of HFD/STZ-induced DN mice and mice treated with acrolein (2.5 mg/kg, p.o.) as shown in FIG. 2A. Compared with the vehicle control group, the blood glucose in the DN group was significantly higher. However, oral gavage of acrolein for 16 weeks did not increase blood glucose compared to that in the control group (FIG. 2B). Similarly, HFD/STZ, but not acrolein, according to glucose intolerance using intraperitoneal glucose tolerance tests (IGTT) (FIG. 2C, 2E). We found that acrolein induced insulin intolerance using insulin tolerance tests (ITT), although the severity was not as high as that in HFD/STZ mice (FIGS. 2D-E).

Figure 2F:
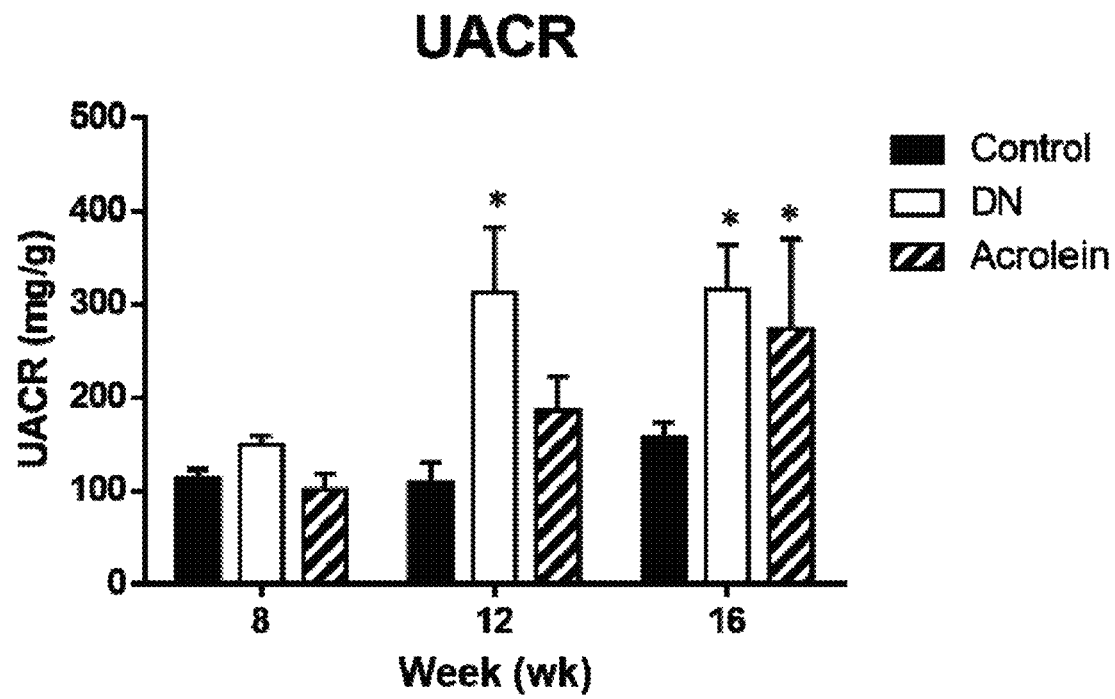
FIG. 2F shows the urine albumin/creatinine ratio (UACR) of the control group, the diabetic nephropathy (DN) group, and the acrolein group after 8, 12, and 16 weeks.
Figure 2G:
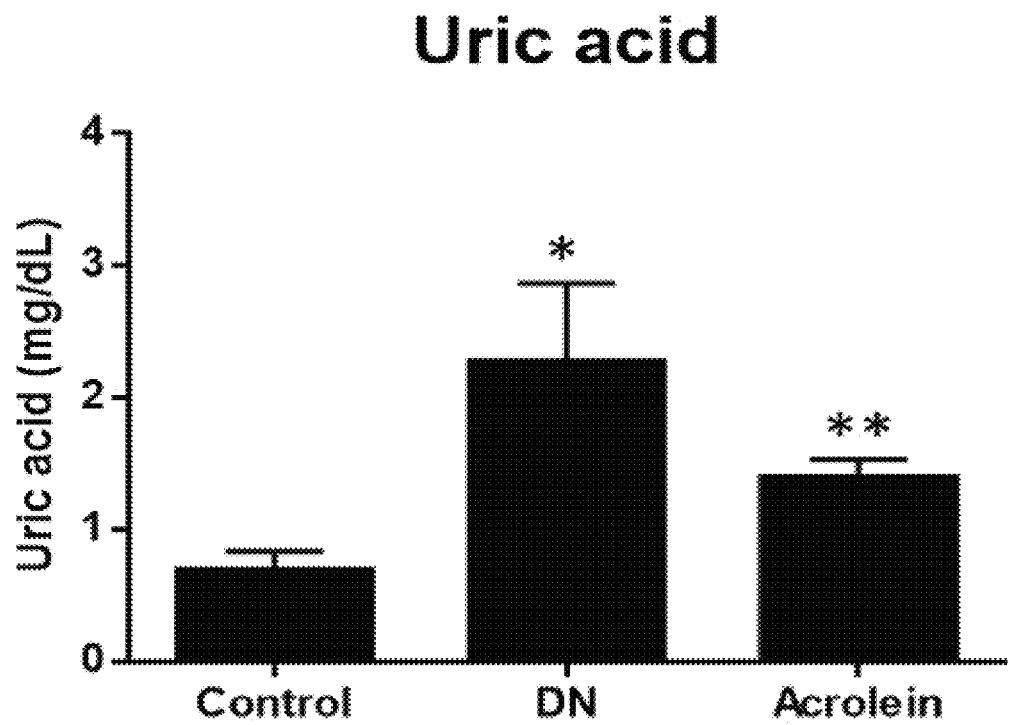
FIG. 2G shows the uric acid (UA) of the control group, the diabetic nephropathy (DN) group, and the acrolein group after 16 weeks.
Figure 2H:
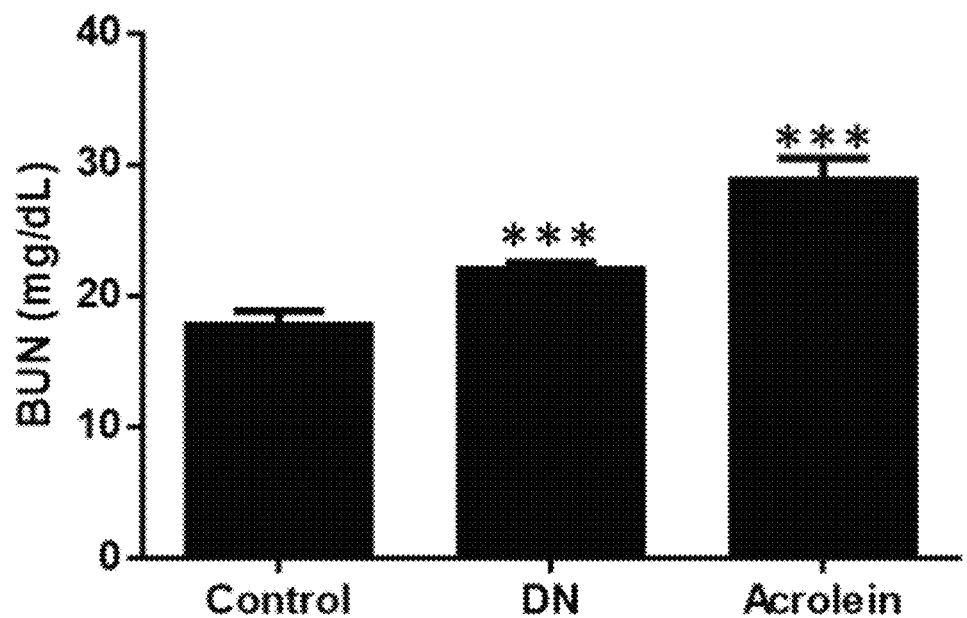
FIG. 2H shows the blood urea nitrogen (BUN) of the control group, the diabetic nephropathy (DN) group, and the acrolein group after 16 weeks.
Figure 2I:
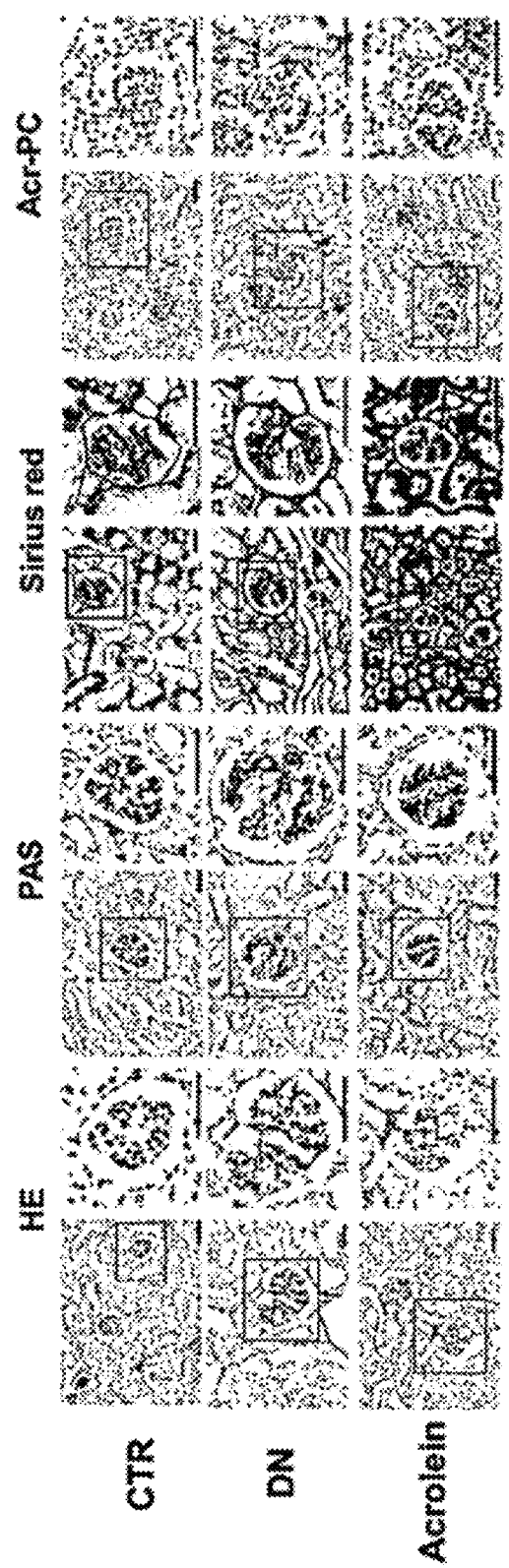
FIG. 2I shows that the kidney histological staining includes hematoxylin and eosin stain (H&E staining), Periodic Acid-Schiff stain (PAS staining), Sirius red and Acr-PC staining.

The HFD/STZ-induced DN mice showed a significant increase in urine albumin/creatinine ratio (UACR) after 12 weeks, indicating a deficiency in renal function (FIG. 2F). On the other hand, oral gavage of acrolein for 12 weeks also increased UACR, although not significantly. Consistently, the HFD/STZ or oral gavage of acrolein for 16 weeks showed a significant increase in UACR, uric acid (UA) and blood urea nitrogen (BUN) compared to those in the control group (FIG. 2F-H). We further explored the pathological abnormalities in HFD/STZ-induced DN mice and acrolein-treated mice. The H&E staining showed that in the control group, the glomerular structure was intact, the proportion of glomerular sacs was normal, and renal tubules were arranged precisely, and there was no inflammatory infiltration in the interstitium (FIG. 2I). In the DN and acrolein groups, there was the disorderly, inflammatory cell infiltration in the interstitium and vacuolar lesion in the epithelial cells (FIG. 2I). PAS staining showed that DN and acrolein groups exhibited glomerular mesangium expansion and extracellular matrix deposition compared with the control group (FIG. 2I). Compared with those in the control group, collagen fiber content and degree of fibrosis in DN and acrolein groups were increased evidently, as shown by Sirius red staining (FIG. 2I). Immunohistochemical staining showed that acrolein-protein conjugate (Acr-PC) were rarely detected in the control group. In contrast, positive staining for Acr-PC was significantly increased in the glomeruli and renal tubules of DN and acrolein groups (FIG. 2I). These results indicate that acrolein plays an essential role in the pathogenesis of HFD/STZ-induced DN.

Example 2

Preparing and Validating the Acr-PC Antibody

Figure 3A:
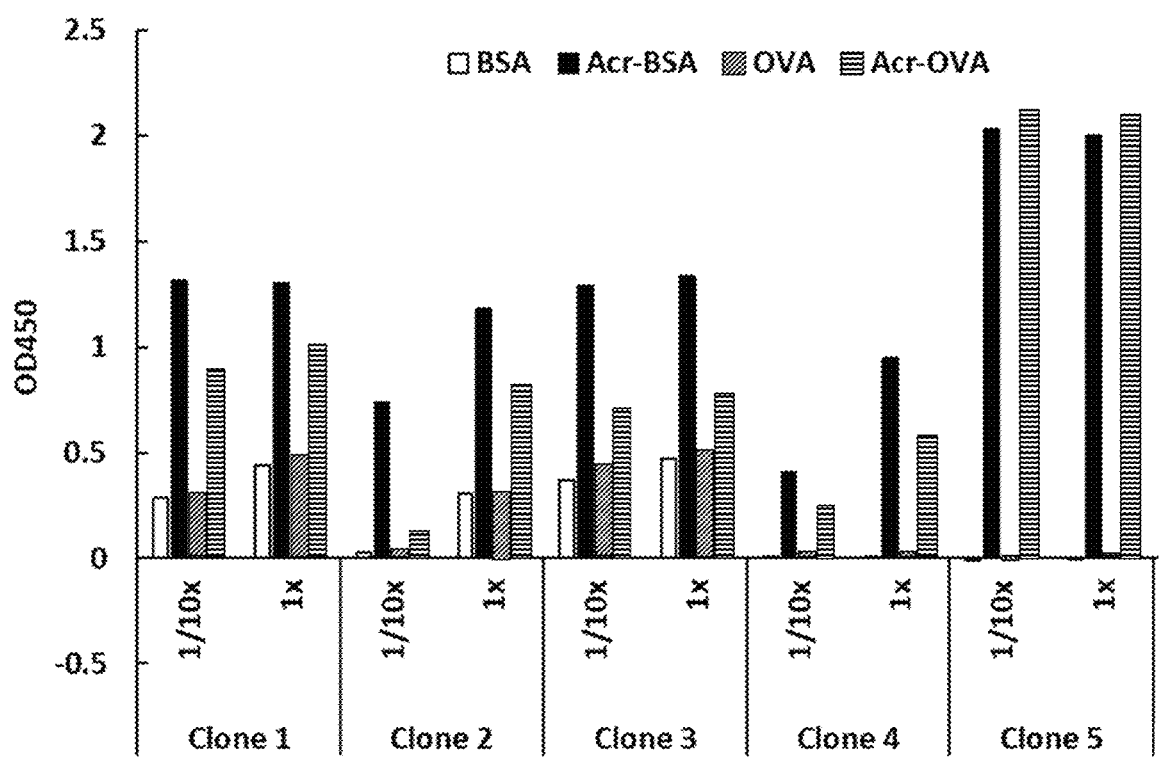
FIG. 3A shows that five Acr-PC antibody-producing hybridoma clones (clone #1 to #5) were obtained after the repeated screening. After the examination of these five clones using an ELISA test against acrolein-modified BSA (Acr-BSA) or acrolein-modified OVA (Acr-OVA), clone #5 showed the most distinctive recognition of Acr-BSA or Acr-OVA.
Figure 3B:
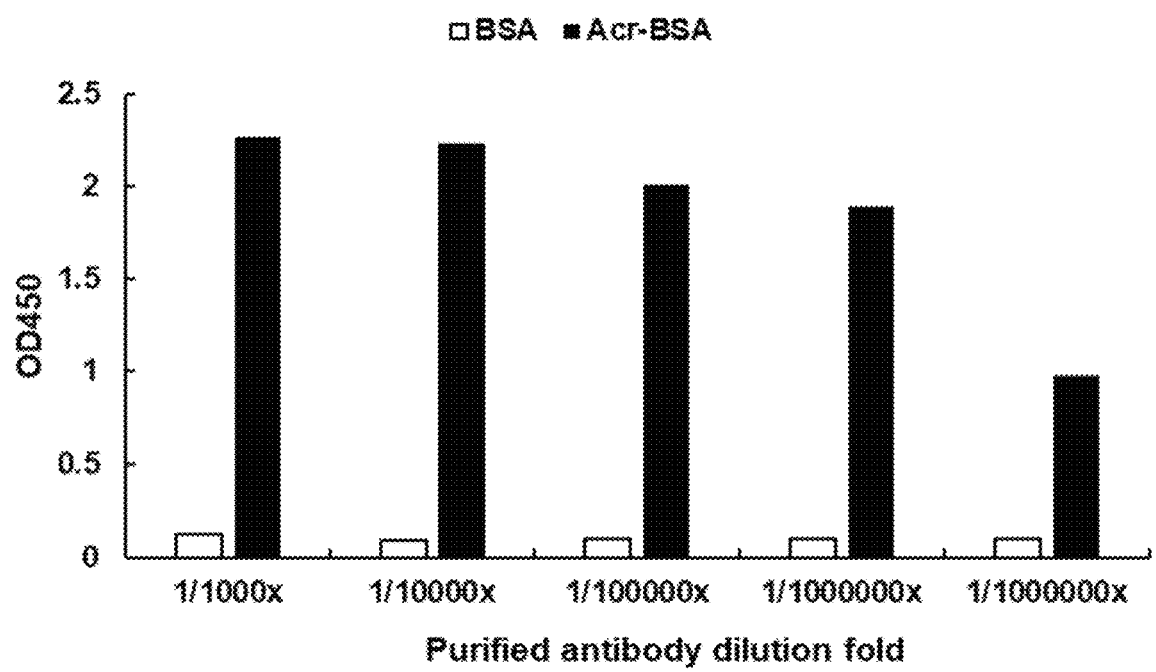
FIG. 3B shows that after antibody purification from hybridoma clone #5, the specificity and the antibody titer were confirmed using a similar ELISA assay. The result showed high specificity and antibody titer.

Monoclonal antibody preparation. Female BALB/c mice were immunized three times with the acrolein-treated ovalbumin (Acr-OVA). Spleen cells from the immunized mice were fused with NS0 murine myeloma cells and cultured in a hypoxantineyamethopterinythymidine selection medium. Culture supernatants of the hybridoma were screened using an ELISA assay, pairs of wells in the microtiter plates on which acrolein-treated BSA (Acr-BSA) was absorbed. After being incubated with 100 μl of hybridoma supernatants and washed with Tris-buffered saline (TBS) containing 0.05% Tween 20 (TBST), the wells were incubated with HRP-conjugated goat anti-mouse IgG, followed by a substrate solution containing TMB. Hybridoma cells corresponding to supernatants that were positive on Acr-BSA or Acr-OVA and negative on BSA or OVA were then cloned by limiting dilutions. After the repeated screening, five clones were obtained. Among them, clone #5 showed the most distinctive recognition of Acr-BSA or Acr-OVA (FIG. 3A). After antibody purification from hybridoma clone #5, we confirmed the specificity and examined the antibody titer using a similar ELISA assay described above. The result showed that the Acr-PC antibody has high specificity and antibody titer (FIG. 3B).

Example 3

Establishment of a Competitive ELISA System for Acrolein-Protein Conjugate (Acr-PC)

Figure 4A:
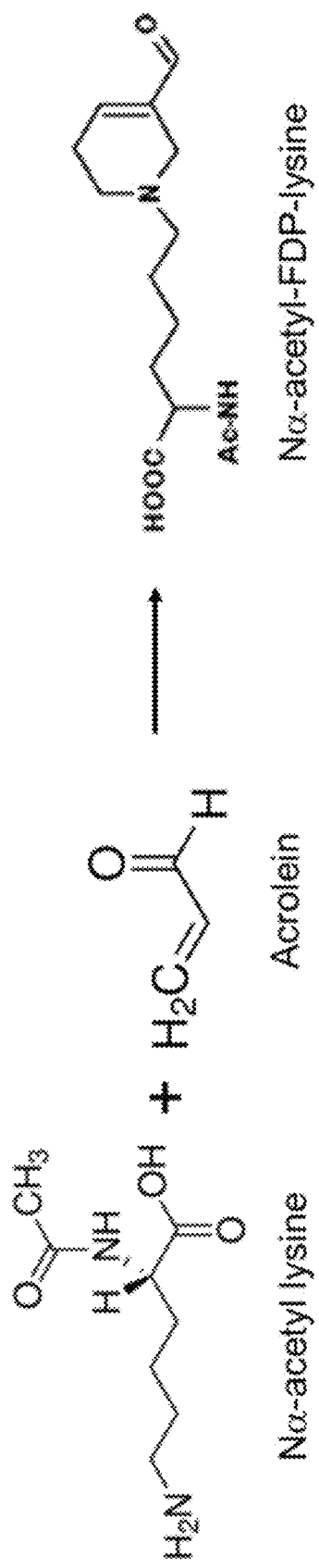
FIG. 4A-4D shows the establishment of a competitive ELISA system for acrolein-protein conjugate (Acr-PC).

Nα-Acetyl-lysine reacts with acrolein to form Nα-acetyl-FDP-lysine as Acr-PC standards (STD) (FIG. 4A).

Figure 4B:
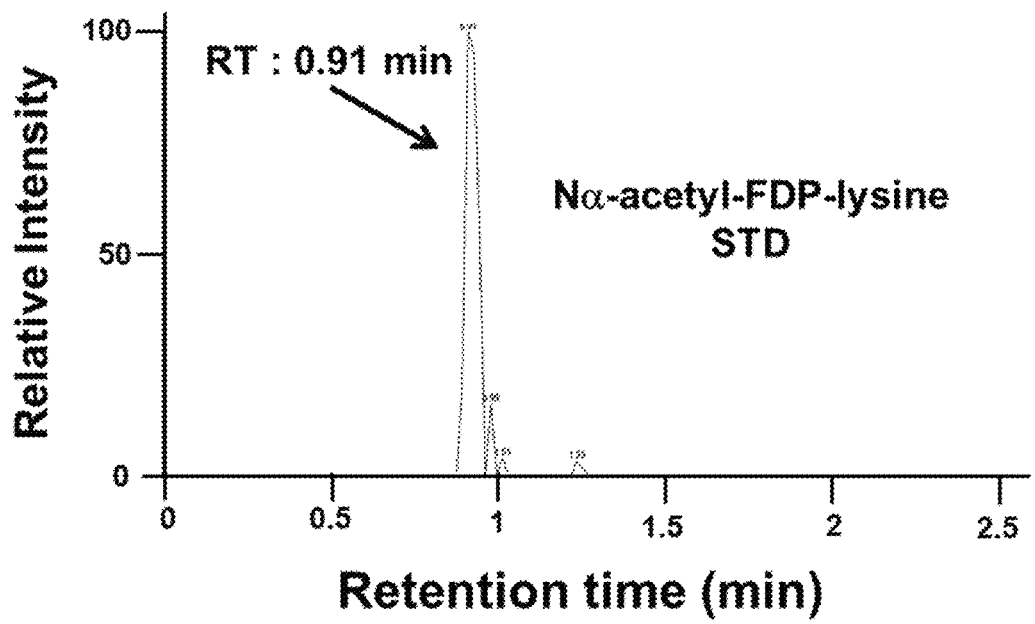
Figure 4C:
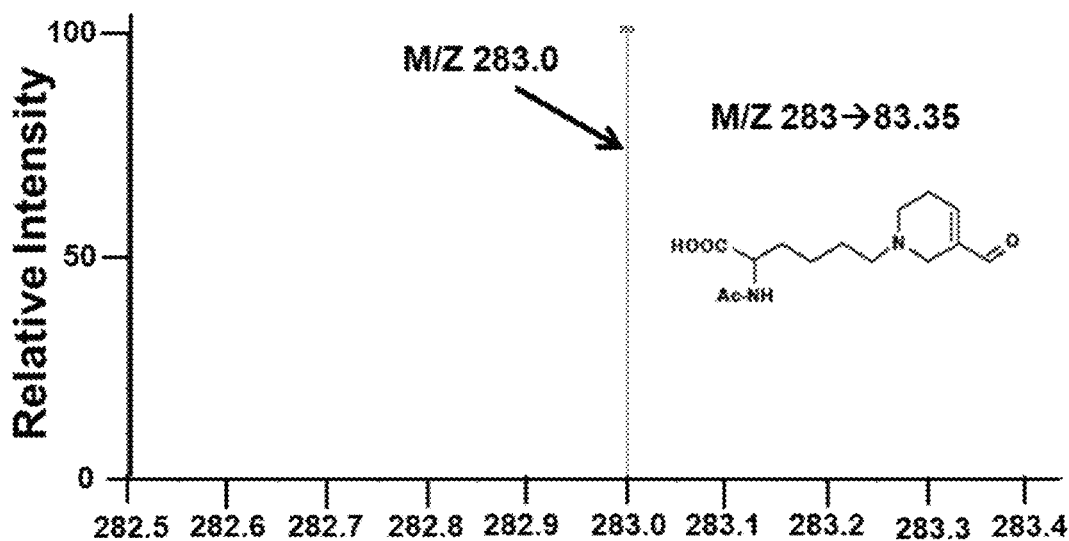

Atypical LC/MS/MS chromatogram for Nα-acetyl-FDP-lysine. Retention time (RT) of the Nα-acetyl-FDP-lysine eluted at 0.91 min. (FIG. 4B) depicts the chromatogram representing the Nα-acetyl-FDP-lysine (283.0→83.35 m/z transition, (FIG. 4C)). The amount of Nα-acetyl-FDP-lysine was calculated by taking the ratio of the two peak areas and multiplying it by the amount of standard.

Figure 4D:
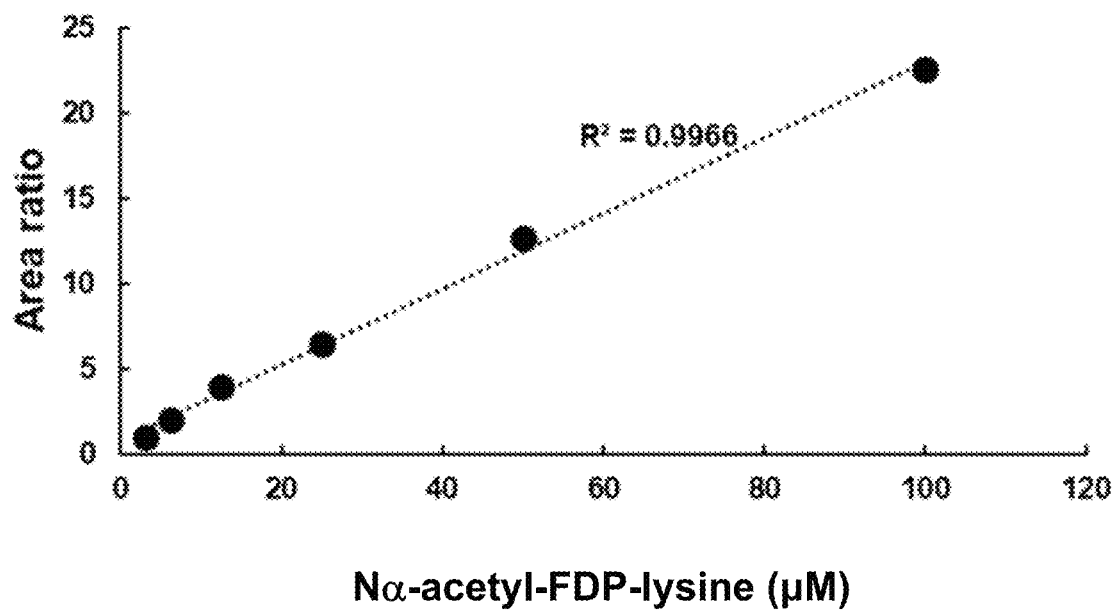

Linear calibration curves of Nα-acetyl-FDP-lysine were obtained using a peak area ratio of 6 standards (3.13, 6.25, 12.5, 25, 50, and 100 µM) as a function of the different concentrations (FIG. 4D).

100-µl aliquot of the antigen solution (Acr-BSA) was added to each well of a 96-well microtiter plate and incubated for 20 h at 4° C. The antigen solution was then removed, and the plate was washed with TBST. Each well was incubated with 100 ul of 1% BSA in TBST for 30 min at 37° C. in a humidified chamber to block the unsaturated plastic surface. The plate was then washed once with TBST. A 100-µl aliquot of competitor/antibody mixtures containing 100 ng/ml Acr-PC antibody and Acr-PC or plasma samples was added to each well and incubated for 1 h at 37° C. The supernatants were discarded, the wells were washed three times with TBST, and 100 µl of a 2000× dilution of HRP-conjugated goat anti-mouse IgG in TBST was added. After being incubated for 1 h at 37° C., the supernatant was discarded, and the plates were washed three times with TBST. Enzyme-linked antibodies bound to the well were revealed by adding 100 µl/well TMB Substrate Solution. The reaction was terminated by adding 50 ul of 2 M sulfuric acid, and the absorbance at 450 nm was read on a micro-ELISA plate reader.

Example 4

Testing Specimens of Subjects and Analyzing the Acr-PC Biomarker

Figure 5A:
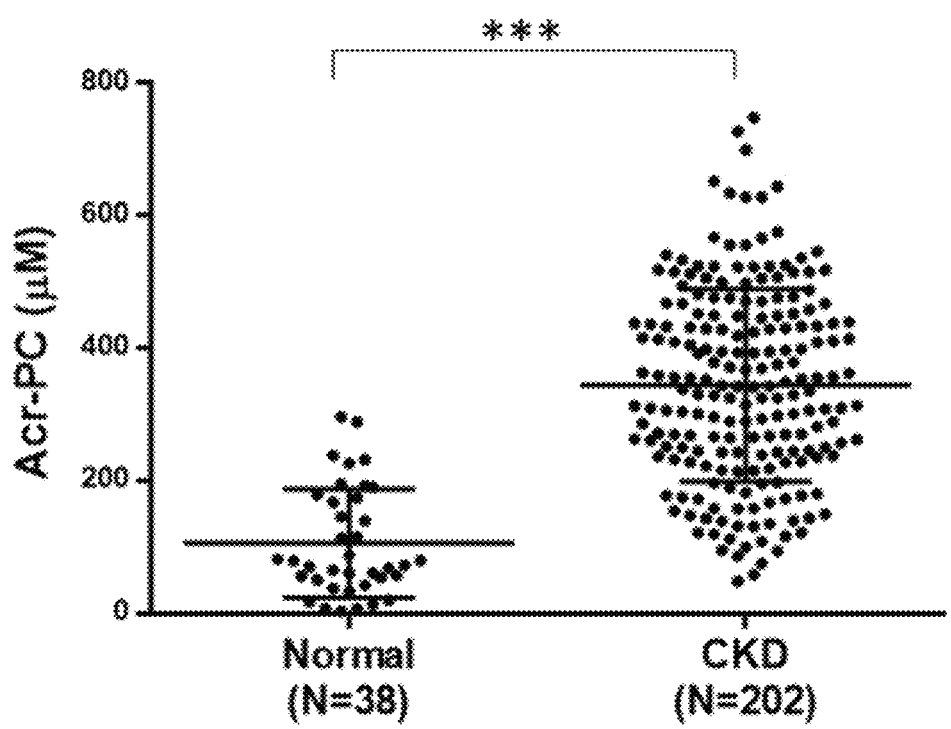
FIG. 5A shows the Acr-PC levels in plasma samples of normal subjects (CTR, N=38) and chronic kidney disease (CKD) patients (N=202).
Figure 5B:
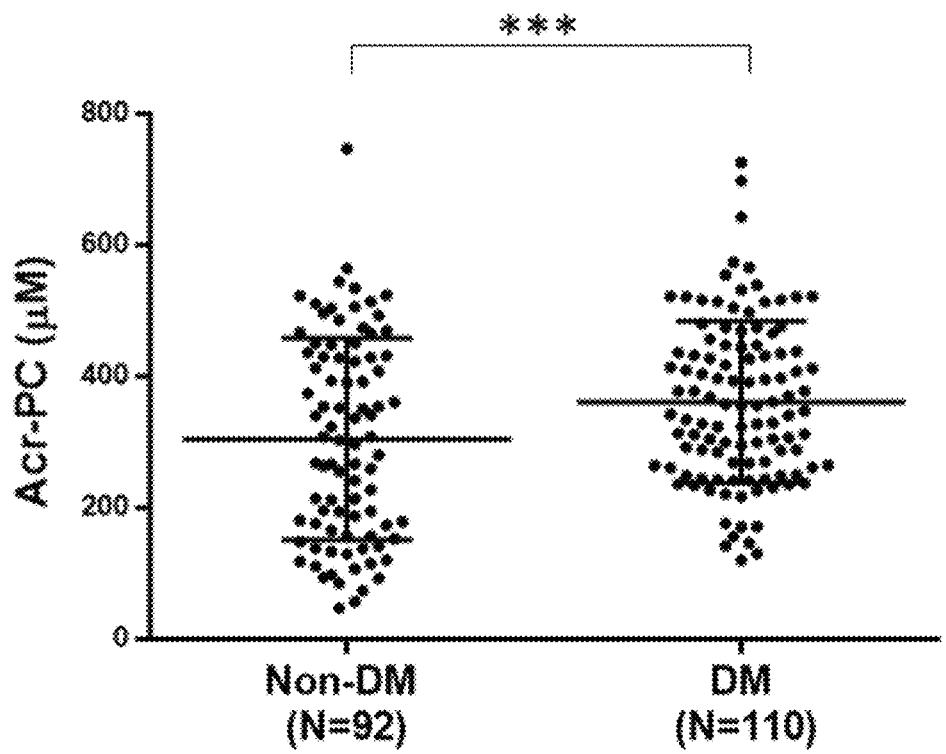
FIG. 5B shows the comparison of plasma Acr-PC levels in CKD patients without DM (N=92) and with DM (N=110).
Figure 5C:
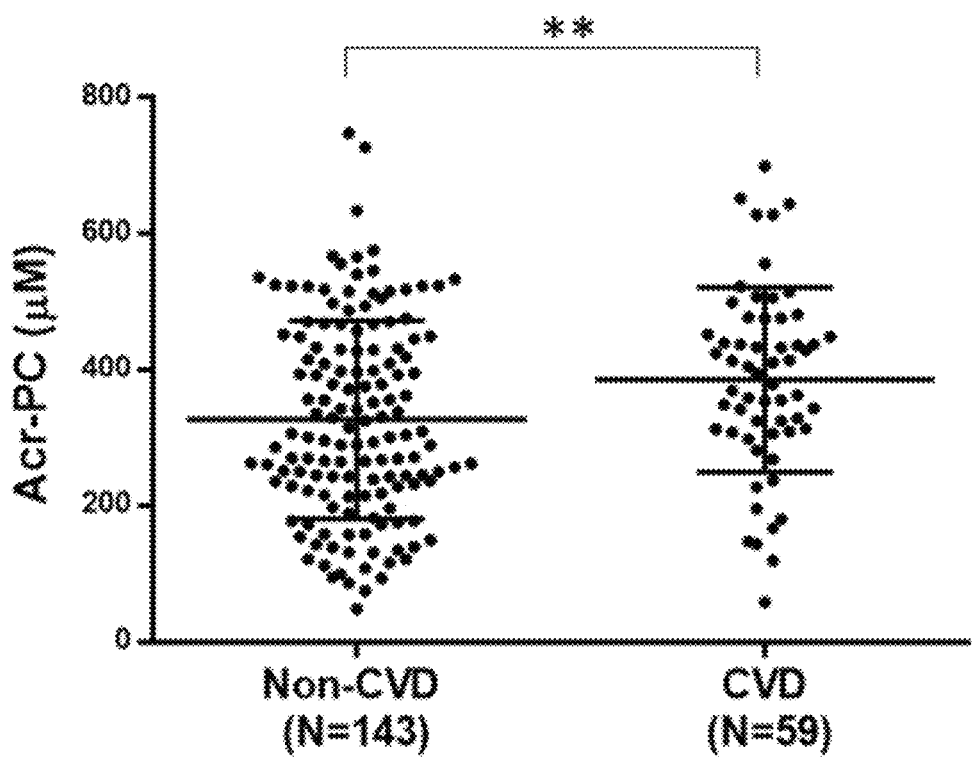
FIG. 5C shows the comparison of plasma Acr-PC levels in CKD patients without CVD (N=143) and with CVD (N=59).
Figure 5D:
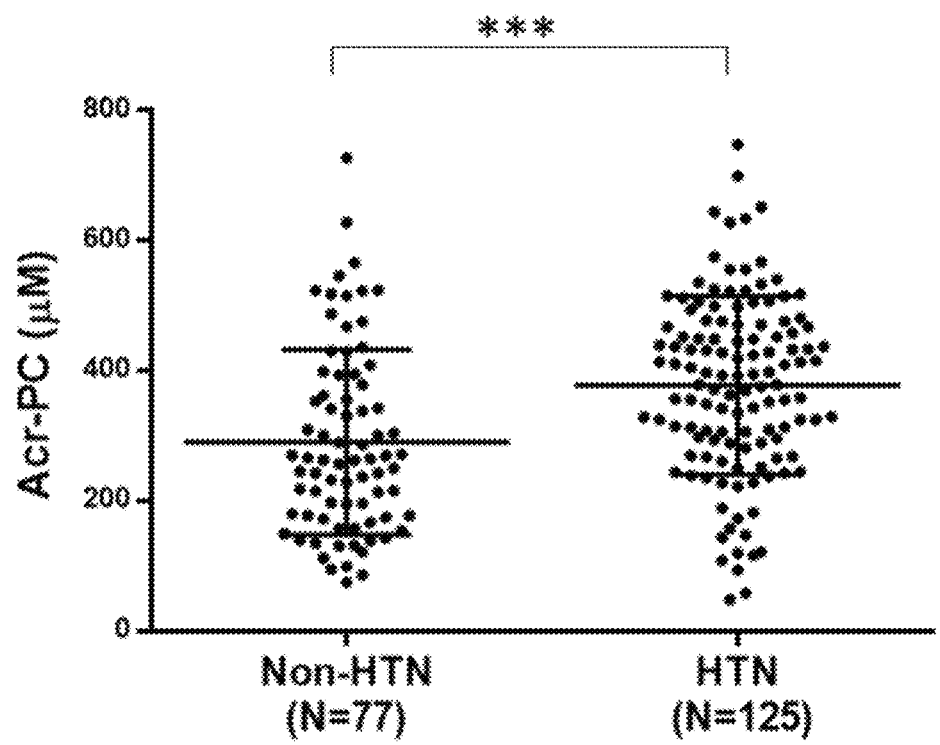
FIG. 5D shows the comparison of plasma Acr-PC levels in CKD patients without HTN (N=77) and with HTN (N=125).
Figure 5E:
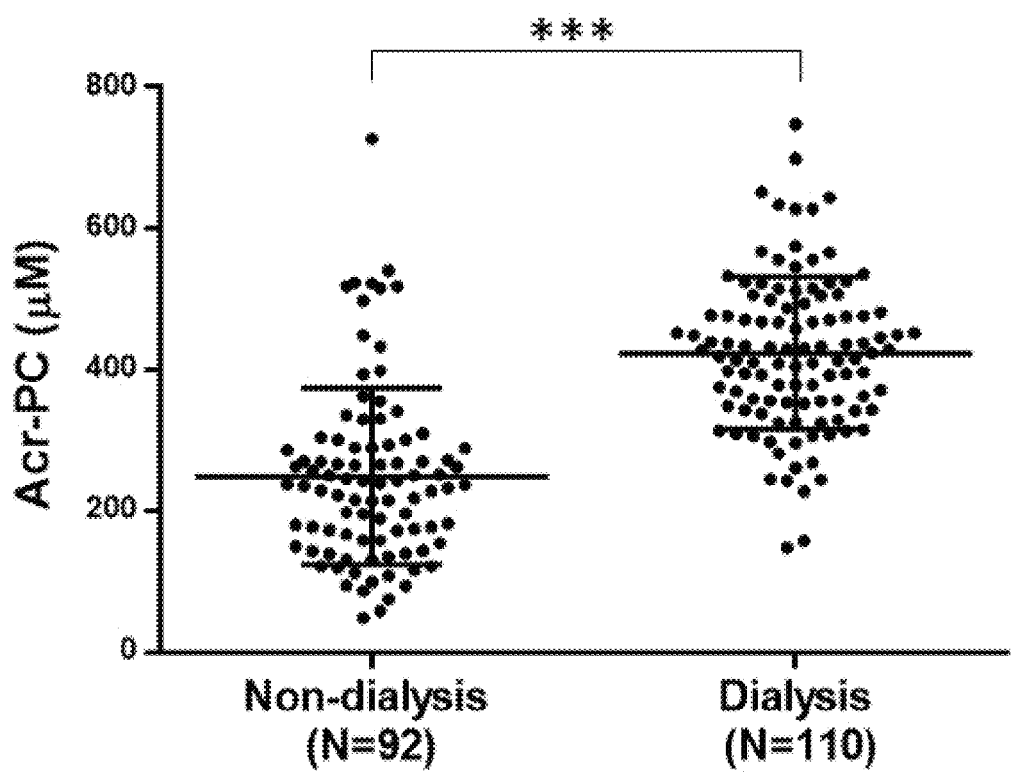
FIG. 5E shows the comparison of plasma Acr-PC levels in CKD patients without dialysis (N=92) and with dialysis (N=110).
Figure 5F:
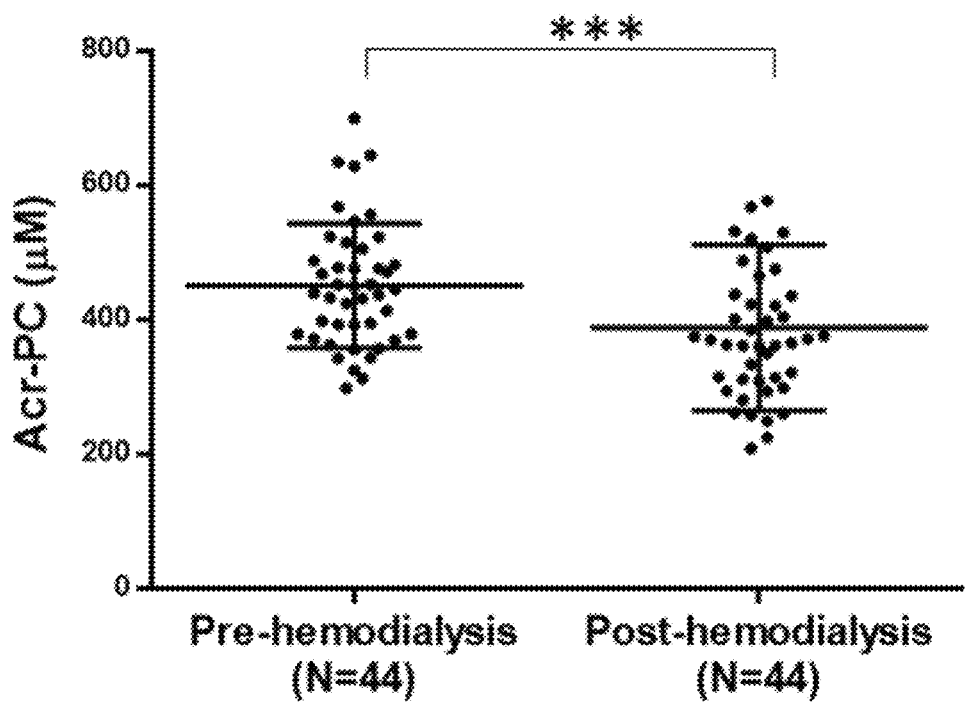
FIG. 5F shows that the Acr-PC levels in plasma samples of 44 ESRD patients were collected before and after hemodialysis.
Figure 5G:
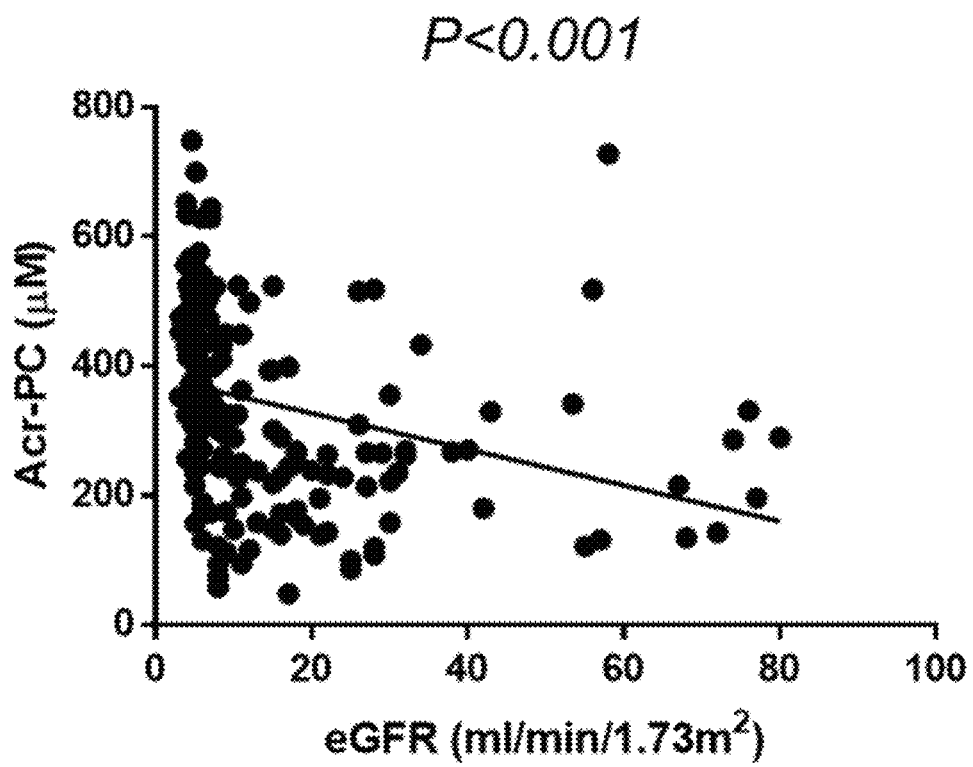
FIG. 5G shows that the correlation between plasma Acr-PC levels and eGFR (estimated Glomerular filtration rate) of 202 CKD patients was evaluated by Pearson correlation analysis.

We recruited 240 subjects, including 38 normal volunteers and 202 CKD patients, from Taipei Veterans General Hospital. Using an established Acr-PC ELISA system, we analyzed Acr-PC levels in plasma samples of these subjects. The results showed increased Acr-PC in CKD patients compared to normal subjects (FIG. 5A), and the plasma Acr-PC levels were significantly increased in CKD patients with DM compared to those without DM (FIG. 5B). Interestingly, we further found that the plasma Acr-PC levels were significantly increased in CKD patients with cardiovascular diseases (CVD) or hypertension (HTN) compared to those without CVD or HTN (FIG. 5C, 5D). Furthermore, significantly increased Acr-PC levels were measured in plasma of CKD patients on dialysis (FIG. 5E), and hemodialysis could significantly decrease Acr-PC levels in plasma samples of these patients (FIG. 5F). We also found that the Acr-PC levels were negatively correlated with estimated glomerular filtration rate (eGFR), a marker for kidney function (FIG. 5G). These results together suggest that plasma Acr-PC levels in DN patients could be potential diagnostic markers.

All examples provided herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority or inferiority of the invention. Although one or more embodiments of the present invention have been described in detail, it should be understood that the various changes, substitutions, and alterations could be made hereto without departing from the spirit and scope of the invention.

It is intended that the specification and examples be considered as examples only, with a true scope and spirit of the invention being indicated by the following claims.

What is claimed is:

1. A kit for diagnosing nephropathy, monitoring the progression of nephropathy, or assessing the therapeutic response of nephropathy, comprising;
   a buffer; and
   an antibody comprising a heavy chain having the amino acid sequence of SEQ ID NO:1 and a light chain having the amino acid sequence of SEQ ID NO:2.

* * * * *